US006447505B2

(12) United States Patent
McGovern et al.

(10) Patent No.: US 6,447,505 B2
(45) Date of Patent: *Sep. 10, 2002

(54) BALLOON CATHETER METHOD FOR INTRA-URETHRAL RADIO-FREQUENCY URETHRAL ENLARGEMENT

(75) Inventors: Francis J. McGovern, Lexington, MA (US); S. Nahum Goldberg, Brookline, MA (US); Eric R. Cosman, Belmont, MA (US); William J. Rittman, III, Lynnfield, MA (US)

(73) Assignees: Cosman Company, Inc., Belmont, MA (US); The General Hospital Corporation, Boston, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/113,683

(22) Filed: Jul. 10, 1998

Related U.S. Application Data

(63) Continuation-in-part of application No. 09/021,802, filed on Feb. 11, 1998.

(51) Int. Cl.⁷ .............................................. A61B 18/14
(52) U.S. Cl. ............................ 606/41; 607/99; 607/113
(58) Field of Search ............................. 606/41, 49, 50; 607/98, 99, 105, 113

(56) References Cited

U.S. PATENT DOCUMENTS

| | | | |
|---|---|---|---|
| 4,411,266 A | 10/1983 | Cosman | 128/303.18 |
| 4,785,823 A | 11/1988 | Eggers et al. | |
| 4,966,597 A | 10/1990 | Cosman | |
| 5,249,585 A | 10/1993 | Turner et al. | 607/99 |
| 5,257,977 A | 11/1993 | Eshel | |
| 5,263,931 A | 11/1993 | Miller | 604/96 |
| 5,300,099 A | 4/1994 | Rudie | 607/101 |
| 5,330,518 A | 7/1994 | Neilson et al. | 607/101 |
| 5,348,554 A | 9/1994 | Imran et al. | 606/41 |

(List continued on next page.)

FOREIGN PATENT DOCUMENTS

| | | | |
|---|---|---|---|
| WO | WO 96-00036 | 1/1996 | |
| WO | WO 96-00039 | 1/1996 | |
| WO | WO 96/34571 | 11/1996 | |
| WO | 96/37158 | 11/1996 | A61B/17/36 |
| WO | 98/27881 | 7/1998 | A61B/17/39 |

OTHER PUBLICATIONS

US 5,326,343, 7/1994, Rudie et al. (withdrawn)

Cosman, Eric R., Ph.D. et al., "Theoretical Aspects of Radiofrequency Lesions in the Dorsal Root Entry Zone," *Neurosurgery*, Dec. 1984; vol. 15, No. 6; pp. 945–950 (Article).

Sunshine, Robert D., M.D., et al., "Complications of Transurethral Resection of the Prostate," *Urologic Complications, Medical and Surgical, Adult and Pediatric*, 1986; Chapter 18; pp. 231–246.

Schulman, Claude C., et al., "Transurethral Needle Ablation (TUNA): Safety, Feasibility, and Tolerance of a New Office Procedure for Treatment of Benign Prostatic Hyperplasia," *European Urology*; Oct., 1993; vol. 24; pp. 415–423.

(List continued on next page.)

*Primary Examiner*—Lee Cohen
(74) *Attorney, Agent, or Firm*—Fish & Richardson P.C.

(57) ABSTRACT

Relief of urethral obstruction is achieved by heat ablation of prostatic tissue by an ablation instrument passed within the urethra to a position in the prostate near the point of urethral obstruction. An electrode is coupled to a high-frequency power supply to ablatively heat the urethra and the prostatic tissue near the urethra. Guidance of the electrode placement may be monitored by an imaging device. The instrument may consist of a catheter with an inflatable balloon structure for positioning the instrument. The temperature of the tissue may be sensed at the electrode to control the high-frequency heating energy and ablation process.

29 Claims, 5 Drawing Sheets

U.S. PATENT DOCUMENTS

| | | | |
|---|---|---|---|
| 5,370,675 A | 12/1994 | Edwards et al. | 607/101 |
| 5,370,677 A | 12/1994 | Rudie et al. | 607/101 |
| 5,403,311 A | 4/1995 | Abele et al. | 606/49 |
| 5,464,437 A | 11/1995 | Reid et al. | 607/101 |
| 5,472,441 A | 12/1995 | Edwards et al. | |
| 5,480,417 A * | 1/1996 | Hascoet et al. | 607/113 |
| 5,486,161 A | 1/1996 | Lax et al. | 604/22 |
| 5,492,529 A | 2/1996 | Neuwirth et al. | |
| 5,520,684 A * | 5/1996 | Imran | 606/41 |
| 5,542,915 A | 8/1996 | Edwards et al. | 604/22 |
| 5,545,137 A | 8/1996 | Rudie et al. | 604/96 |
| 5,545,161 A * | 8/1996 | Imran | 606/41 |
| 5,599,294 A | 2/1997 | Edwards et al. | 604/22 |
| 5,599,346 A | 2/1997 | Edwards et al. | 606/41 |
| 5,620,480 A | 4/1997 | Rudie | 607/101 |
| 5,628,770 A | 5/1997 | Thome et al. | 607/101 |
| 5,630,426 A | 5/1997 | Eggers et al. | |
| 5,645,528 A | 7/1997 | Thome | 604/96 |
| 5,681,282 A | 10/1997 | Eggers et al. | 604/114 |
| 5,733,316 A | 3/1998 | Tierney et al. | 607/101 |
| 5,755,754 A * | 5/1998 | Rudie et al. | 607/101 |
| 5,849,011 A | 12/1998 | Jones et al. | 606/47 |
| 6,171,306 B1 | 1/2001 | Swanson et al. | |

OTHER PUBLICATIONS

Goldwasser, B., et al., "Transurethral Needle Ablation (TUNA) of the Prostate Using Low–Level Radiofrequency Energy: An Animal Experimental Study," *European Urology*; Oct., 1993; vol. 24; pp. 400–405.

Onik et al., "Transrectal Ultrasound–Guided Percutaneous Radical Cryosurgical Ablation of the Prostate," *Cancer*; Aug. 15, 1993; vol. 72, No. 4; pp. 1291–1299.

Goldberg, Nahum S., et al., "Hepatic Metastases: Percutaneous Radio–Frequency Ablation with Cooled–Tip Electrodes," *Radiology*; Nov., 1997; vol. 205, No. 2; pp. 367–373.

Blute, Michael L., et al., "Transurethral Microwave Thermotherapy for Management of Benign Prostatic Hyperplasia: Results of the United States Prostatron Cooperative Study," *Journal of Urology*; Nov., 1993; vol. 150, No. 5, Part 2 of 2; pp. 1591–1596.

Goldberg, Nahum S., et al., "Tissue Ablation with Radiofrequency: Effect of Probe Size, Gauge, Duration, and Temperature on Lesion Volume," *Academic Radiology*; May, 1995; vol. 2, No. 5; pp. 399–404.

Bhanot, et al. "A Radiofrequency Method of Thermal Tissue Ablation for Benign Prostatic Hyperplasia," *Urology*, Mar. 1995, 45:427–433.

Cosman, et al. "Theoretical Aspects of Radiofrequency Lesions in the Dorsal Root Entry Zone," *Neurosurgery*, 15:945–950 (1984).

Dawkins, et al. "Radiofrequency heat–treatment to the prostate for bladder outlet obstruction associated with benign prostatic hyperplasia: a 4–year outcome study," *British Journal of Urology*, 79:910–914 (1997).

Djavan, et al. "Minimally Invasive Procedures and Medical Management—Their Relative Merits in Treating Lower Urinary Tract Symptoms of Benign Prostatic Hyperplasia", Reviews in Urology, 2:105–114 (2000).

Thermex Clinical Data, Direx Medical Systems, Nov. 1993.
Turapy Clinical Data, Direx Medical Systems, undated.

* cited by examiner

BALLOON CATHETER METHOD FOR INTRA-URETHRAL RADIO-FREQUENCY URETHRAL ENLARGEMENT

CROSS-REFERENCE TO RELATED APPLICATIONS

This application is a continuation-in-part of application Ser. No. 09/021,802, filed on Feb. 11, 1998, entitled "METHOD AND SYSTEM FOR PERFORMING INTRA-URETHRAL RADIO-FREQUENCY URETHRAL ENLARGEMENT."

FIELD OF THE INVENTION

This invention relates generally to advances in medical systems and procedures for prolonging or improving human life. More particularly, this invention relates to an improved method and system for alleviating urinary obstruction caused by enlargement of the prostate by performing intra-urethral radio-frequency ablation for urethral enlargement.

BACKGROUND OF THE INVENTION

A majority of all males over 60 years old experience partial or complete urinary obstruction because of enlargement of the prostate. This condition usually originates from benign prostatic hyperplasia (BPH), which is an increase in cell mass near the urethra, or less likely, from prostate cancer. Both these conditions involve an increase in prostatic tissue mass, which in its increased state encroaches on the urethra and obstructs the urinary pathway.

In the case where urinary obstruction is caused by BPH, a common treatment involves a medical procedure using a medical side-cutting instrument and/or endoscope to surgically enlarge a passageway for urine flow through the prostate. The side-cutting instrument or an endoscope is passed through the penis into the urethra and is surgically used to remove prostate tissue and part of the urethra at the point of obstruction. This procedure is referred to as "Trans-urethral Resection of the Prostate" (or "TURP").

This procedure, although effective, is invasive and complicated. For example, it requires the use of anesthesia and substantial hospital care. It also has the risk of causing bleeding. Moreover, it is expensive and causes great discomfort and trauma to the patient. For example, chapter 18, entitled "Complications of Transurethral Resection of the Prostate," by R. Sunshine and M. Droller, of a book entitled *Urologic Complications, Medical and Surgical, Adult and Pediatric*, edited by Fray S. Marshall (Yearbook Medical Publishers, 1986), elaborates on the various complications of the TURP procedure.

In the case where urinary obstruction results from prostatic cancer, surgical prostatectomies are commonly used to eliminate the obstruction. However, surgical prostatectomies have serious side effects and risks, including impotence and urinary incontinence.

In recent years, less invasive systems and procedures that inflict less trauma on patients have been attempted. one such procedure, called "Trans-urethral Needle Ablation" (or "TUNA"), involves passing a radio-frequency (RF) instrument such as a catheter, cannula, sheath, or scope into the urethra. The RF instrument houses special RF electrode tips that emerge from the side of the instrument. The tips are pushed out of the instrument along off-axis paths to pierce the urethral wall and pass into the prostatic tissue outside of the urethra. As a result of the various electrodes emerging from the side of the instrument, such radio-frequency instruments are frequently complex and expensive.

By heating the prostate with RF power applied through the electrode tips emerging from the side of the radio-frequency (RF) instrument, the prostate tissue surrounding the urethra is ablated. Specifically, heat ablation is performed at multiple locations outside the urethra to provide a series of ablations, thereby causing the prostate tissue outside the urethra to die and necrose. Subsequent to heating, the necrotic tissue is absorbed by the body or excreted, thereby reducing the tissue mass outside the urethra, which consequently reduces the urethral obstruction.

For further explanation of this system and procedure, one can consult a research paper published by Goldwasser et al., entitled "Transurethral needle ablation (TUNA) of the prostate using low-level radio-frequency energy: an animal experimental study;" *Eur. Urol.*, vol. 24, pp. 400–405 (1993); and a research paper published by Schulman, et al., entitled "Transurethral needle ablation (TUNA); safety, feasibility, and tolerance of a new office procedure for treatment of benign prostate hyperplasma;" *Eur. Urol.*, vol. 24, pp. 415–423 (1993). Also, product literature on the TUNA system available from a company named Vitamed, Inc., of Menlo Park, Calif., carries some description of the procedure.

The TUNA system and procedure is generally used to relieve urethral obstruction caused by BPH. It favors a transurethral approach because the target tissue to be ablated is generally near to it. However, again, although the TUNA system and procedure is effective, it requires epidural or general anesthetic, and generally causes the patient great discomfort and pain. Moreover, the TUNA procedure is medically and technically very complex for surgeons to perform, requiring a complicated and expensive catheter or sheath or RF electrode system to perform it. Also, it is a relatively blind procedure in the sense that the ends of the RF electrodes emerging at the side of the radio-frequency electrode system, once they penetrate the target tissue, cannot be seen. Nor is there any technique for providing a visual representation of them. Furthermore, the TUNA system and procedure attempts to leave the urethra intact and uninjured by the application of RF heating, which is difficult to achieve, making its outcome uncertain. The TUNA system and procedure causes scratching of the urethra, bleeding or irritation from a cystoscope, cannula, catheter, or tissue-piercing electrode tips passed into the urethra. Furthermore, the TUNA procedure produces trapped coagulated and necrotic tissue or fluid in the interstitial region of the prostate outside the urethra. This can result in swelling and increased pressure of tissue outside the prostate as the necrotic tissue is absorbed by the body. Such pressure can compress the urethra to further enhance its obstruction.

It is observed that such techniques have not been directed at creating ablation of urethra or the periurethral region (the region surrounding the urethra or the critical prostate region) for the reasons discussed above. Accordingly, it would be desirable to have an effective technique to perform intra-urethral RF electrode ablation of the urethra and periurethral tissue for the purposes of alleviating urinary obstruction caused by enlargement of the prostate and that avoids the limitations of the art.

Another system and procedure contemplated by Onik et al. is described in their research paper entitled "Transrectal ultrasound-guided percutaneous radical cryosurgical ablation of the prostate;" *Cancer*, vol. 72, pp. 1291–1299 (1993). This technique is utilized for the treatment of prostate cancer and involves disposing cryogenic (freezing) probes in the prostate for ablating the cancer cells. Onik et al. propose passing a cryogenic probe transperineally (through the perineum) into the prostate. At the same time, an imaging ultrasonic probe is passed through the rectum and is used to visualize the position of the cryogenic probe and the volume of cryogenic ablation in the prostate. This technique requires use of cryogenic probes (also referred to as cryo-probes) having relatively large diameters. The cryo-probes are complex in construction and operation and require elaborate cooling and thawing cycles, making the procedure typically quite complicated and expensive. It is technically challenging and critical to maintain precise temperatures at the target tissue area to prevent hemorrhaging when removing the probe and also to prevent freezing sensitive rectal mucosa tissue.

One more recent procedure contemplated and reported by McGahan, et al., in their research paper entitled "Percutaneous Ultrasound-Guided Radio-frequency Electrocautery Ablation of Prostate Tissue in Dogs," *Acad. Radiol.*, pp. 61–64 (1994), involves placing an RF electrode transrectally into the prostate of a dog under rectal ultrasound guidance. Their intent was solely to explore the feasibility of ablating cancerous tumors within the peripheral region of the prostate. Their research treated only normal animals and no ablation of cancer tissue was actually performed. McGahan et al. hoped to prevent RF heat ablation of the urethra (which is located centrally in the prostate). To achieve their objective, they suggested that the urethra should be irrigated with saline solution, using a catheter, to prevent RF heat damage to the urethra and periurethral tissue. They concluded that their system and procedure was impractical for ablating prostate cancer cells, because the RF lesions were limited to 1 to 1.5 cm in diameter, which they felt would be too small to adequately treat malignant cancer cells.

Generally, prostate cancer primarily occurs in the peripheral (non-central) zone of the prostate. It is often multi-focal, near the rectal wall, and near nerves controlling potency. Recognizing the restraints and delicate circumstances, McGahan et al., were discouraged by the results of their research. They concluded that their technique may be applicable to only a small percentage of prostate carcinomas, specifically those that are small and can be imaged by ultrasound. In their paper, they emphasized their concern for preventing RF heat damage to the rectal mucosa tissue. Thus, as a result of their efforts to treat prostate cancer, which is predominantly located in the peripheral non-central part of the prostate, they focused their research efforts on the peripheral, peri-rectal regions of the prostate. Their research did not contemplate RF ablation in the central periurethral region to produce an ablation cavity near the urethra or to ablate the urethra itself. In fact, they explicitly sought to avoid injury of the urethra by avoiding treatment of periurethral tissues. Their method and objectives were directed to cancer and were found to be disadvantageous for treatment of BPH or for treating urethral or periurethral tissues by radio-frequency (RF) ablation to relieve urinary obstruction.

It should be recognized that the theory behind and practice of RF heat lesion has been known for decades, and a wide range of RF generators and electrodes for accomplishing such practice exist. For example, equipment for performing heat lesions is available from Radionics, Inc., located in Burlington, Massachusetts. Radio-frequency (RF) ablation is well known and described in medical and clinical literature. To that end, a research paper by E. R. Cosman, et al., entitled "Theoretical Aspects of Radio-frequency Lesions in the Dorsal Root Entry Zone;" *Neurosurgery*, vol. 15; no. 6, pp. 945–950 (1984), describing various techniques associated with radio-frequency lesions, is incorporated herein by reference. Also, a research paper by S. N. Goldberg, et al., entitled "Tissue Ablation with Radio-frequency: Effect of Probe Size, Gauge, Duration, and Temperature on Lesion Volume;" *Acad. Radiol.*, vol. 2; pp. 399–404 (1995), describes techniques and considerations relating to tissue ablation with radio-frequency energy.

In addition, a paper by S. N. Goldberg, et al., entitled "Hepatic Metastases: Percutaneous Radio-Frequency Ablation with Cooled-Tip Electrodes," *Radiology*, vol. 205, no.2, pp. 367–373 (1997), describes various techniques and considerations relating to tissue ablation with radio-frequency electrodes having cooled electrode tips. Cooled ablation electrodes will maintain tissue near the electrode at lowered temperatures which are below ablation temperatures. Cooling of the urethra by a catheter is suggested by McGahan et al., cited above, to prevent RF heat damage to the urethra and periurethral tissue.

Generally, cooled radio-frequency electrodes having an elongated shaft or catheter structure have cooling channels within the electrode structure. These cooling channels, for example, may comprise a first channel to carry cooled fluid from an external source, which is connected to the electrode at its proximal end. The coolant fluid is carried through the first channel to provide cooling to the electrode end, which is typically near the distal end of the electrode structure. The electrode structure typically also comprises a second channel within the electrode structure that is connected near the distal end to the first channel and which is adapted to bring the cooling fluid from the distal electrode region back to the source. Such recirculating channels for cooling fluid move the cooled fluid in one direction from the fluid source to the electrode and then back to the source. For a self-contained, internally cooled, electrode structure, the cooling channels would be inside the structure and sealed from other channels that may exist within the catheter such as for urinary drainage or for inflation of a balloon tip. Thus cooled electrode structures add a complexity of structure compared to non-cooled electrode structures.

Use of cooled ablation devices placed inside the urethra would have the objective of sparing the urethra from heat damage during the time when heating of prostatic tissue is occurring at a distance from the urethra.

Transurethral microwave thermotherapy (or "TUMT") has been used to treat BPH and illustrates the use of a cooled catheter which also delivers heat energy to the prostate. A catheter which has a microwave probe inside it is inserted into the urethra to the point of the prostate. The microwave probe is typically a microwave antenna which is located inside the catheter near its distal end and is connected to an external generator of microwave power output. In this way the prostate is heated by radiative electromagnetic heating. At the same time the catheter is cooled by circulation of a coolant fluid within the catheter. The objective is, as stated above, to cool the urethra and thereby prevent damage to it by the heating process which is occurring in prostatic tissue that is outside of and at a distance from the urethra. Thus, the TUMT procedure seeks to preserve the urethra and the prostate tissue immediately outside the urethra by cooling the catheter with fluid coolant that is circulated within the catheter. In TUMT, the microwave antenna is located inside the catheter and not in conductive electrical contact with the urethra. The microwave heating in the TUMT procedure occurs in the prostatic tissue located at a distance away from the urethra as a result of the simultaneous cooling action of the channels within the catheter and the deposition of microwave power into the prostate tissue from the radiated energy from the antenna. Thus the prostatic tissue immediately around the urethra and the urethra itself are deliberately spared from receiving an ablative level of heating in the TUMT procedure. Further explanation of the TUMT system and procedure can be found in the paper by Blute, et al., entitled "Transurethral microwave thermal therapy for the management of benign prostatic hyperplasia: results of the United States prostration cooperative study." *J. Urol.*, vol. 150, pp. 1591–1596 (1993).

However, for reasons described above, such techniques have never been performed to ablate the periurethral region and the urethra itself using an intra-urethral RF electrode that does not pierce the urethra. Accordingly, an effective technique for performing intra-urethral RF electrode ablation to achieve urethral enlargement is desirable for purposes of alleviating urinary obstruction caused by enlargement of the prostate.

SUMMARY OF THE INVENTION

The present invention is directed to a system and procedure for radio-frequency (RF) heat ablation of prostatic tissue through the use of an RF electrode, which is advanced into the urethra through the penis and positioned intra-urethrally (within the urethra). The ablation is performed for the treatment of benign prostatic hyperplasia (BPH) and the associated alleviation of urethral obstruction. It would also be used for other diseases such as prostate cancer to relieve urethral obstruction. The system and procedure of the present invention are different from any of the systems and procedures discussed in the background section. The advantages of the present system and method reside in their combined simplicity, economy, control, consistency, enablement of good ablation position and shape, and clinical effectiveness.

As one example, urinary bladder outlet obstruction can be effectively treated using the present system and technique, which is minimally invasive. The technique of the present invention involves inserting an RF electrode into the urethra to the region of urethral obstruction in the prostate. The conductive portion of the RF electrode remains within the urethra. This avoids the more difficult and uncomfortable transurethral approach of the TUNA system procedure discussed above, and may be done without need for passing one or more side-outlet RF electrodes through the urethral wall (via a transurethral approach) into the prostatic tissue surrounding the urethra. In various embodiments, the present system and procedure may include image guidance, which may be performed in a variety of ways including ultrasound, CT, MRI, fluoroscopy, X-rays, or other well known imaging techniques.

In accordance with one embodiment of the invention, an RF electrode may comprise a flexible rubber urethral catheter having an inflatable balloon tip and urinary drainage channel. An electrically conductive RF surface-mounted electrode is attached to the catheter proximal to the balloon portion. This RF electrode can contact electrically the urethral tissue when the catheter is inserted through the penis into the urethra. The balloon may be inflated when the distal portion of the catheter is within the patient's bladder thereby enabling the catheter and the electrode portion to be fixed in a desired position relative to the prostate and urethra. The RF electrode may be determined to be at a desired position in the prostate by a simple traction of the balloon on the bladder. This also ensures against migration or change of position of the electrode from its proper position relative to the prostate and critical structures. X-ray, fluoroscopic, ultrasound, CT, or MRI imaging information can be made of the position of the electrode within the prostate and urethra.

An electrical connection is made from the RF electrode to an RF power generator external to the patient's body. The output from the generator is used to heat and thus ablate the urethral tissue and surrounding prostatic tissue near the RF electrode location. This creates a cavity and expanded opening of the urethra to relieve the urinary obstruction caused by BPH or other prostatic disease.

In contrast to the TUNA technique, the RF electrode of the present invention can be used without piercing the urethra. It enables patients who cannot tolerate the TUNA system and procedure to receive RF ablation treatment. For example, such patients could be those requiring anti coagulation medication for cardiac or neurological problems who should not risk bleeding from a punctured urethra.

In a technique performed according to the present invention, an RF heat lesion is made to ablate the urethra and the periurethral-region (i.e., tissue near or on the urethral tube) to induce necrosis of the prostate tissue near the urethra and of the urethra itself. This induces a symmetric cavity to be formed via obliteration of the urethra and the central region of the prostate in the patient's body a few days after the procedure is performed. The cavity provides direct communication to and widening of the urethral channel. In accordance with one embodiment of the invention, lesion sizes of 1 to 2 cm diameter can be made, which thereafter induce similar sized cavities to be formed, thereby enlarging the urethral passage. These exemplary lesion sizes, similar to those made by the TURP procedure, have proven to be adequate to provide relief from BPH.

It should be noted that in contrast to McGahan et al.'s conclusion that such lesion sizes are inadequate for the ablation of prostate carcinomas, the lesion sizes are adequate in treating BPH.

Also, the present technique avoids the need to observe McGahan et al.'s admonition to avoid heat injury of the urethra, and corresponding necessity for the irrigation and cooling of the urethra as suggested by the article by McGahan et al. By ablating the urethra itself, the present technique has the added advantage of avoiding the possibility of necrotic tissue and liquid becoming entrapped outside the urethra if the urethra is left intact, as in the case of the TUNA and McGahan et al. procedures.

The system and procedure of the present invention differs from TUMT techniques which seek to preserve the urethra by fluid cooling within the electrode catheter. The present technique seeks to ablate a portion of the urethra and periurethral tissue and so directly widen the urethral channel. The present technique has the advantage over the TUMT technique of not requiring added coolant-carrying channels within the catheter which increase complexity and cost of the TUMT electrode systems. The electrodes of the present invention are also simpler than the TUMT devices. The present invention involves a simply constructed RF electrode that makes direct electrical contact with the urethra as compared to an internally located and complex microwave antenna structure in the case of the TUMT device.

The system and method of the present invention has the further advantage of increased simplicity, safety, and economy. The electrode structure is of a simple construction and geometry in one form not requiring coolant channels (although other versions can be made with cooling channels). This has the advantage that the catheter and electrode are easy to construct and therefore economical. It can be inserted easily by any urologist or clinical assistant. Also, it is well tolerated by patients, even those who are in frail health. It is safe, because the simple use of the inflatable balloon within the urethra combined with catheter traction and X-ray imaging with contrast injection assures the correct positioning of the conductive RF electrode within the urethra and prostate.

These features and advantages as well as others of the present method and system will become apparent in the detailed description that follows.

BRIEF DESCRIPTION OF THE DRAWINGS

In the drawings, which constitute a part of the specification, embodiments exhibiting various forms and features hereof are set forth, specifically.

DETAILED DESCRIPTION OF THE INVENTION

Figure 1:
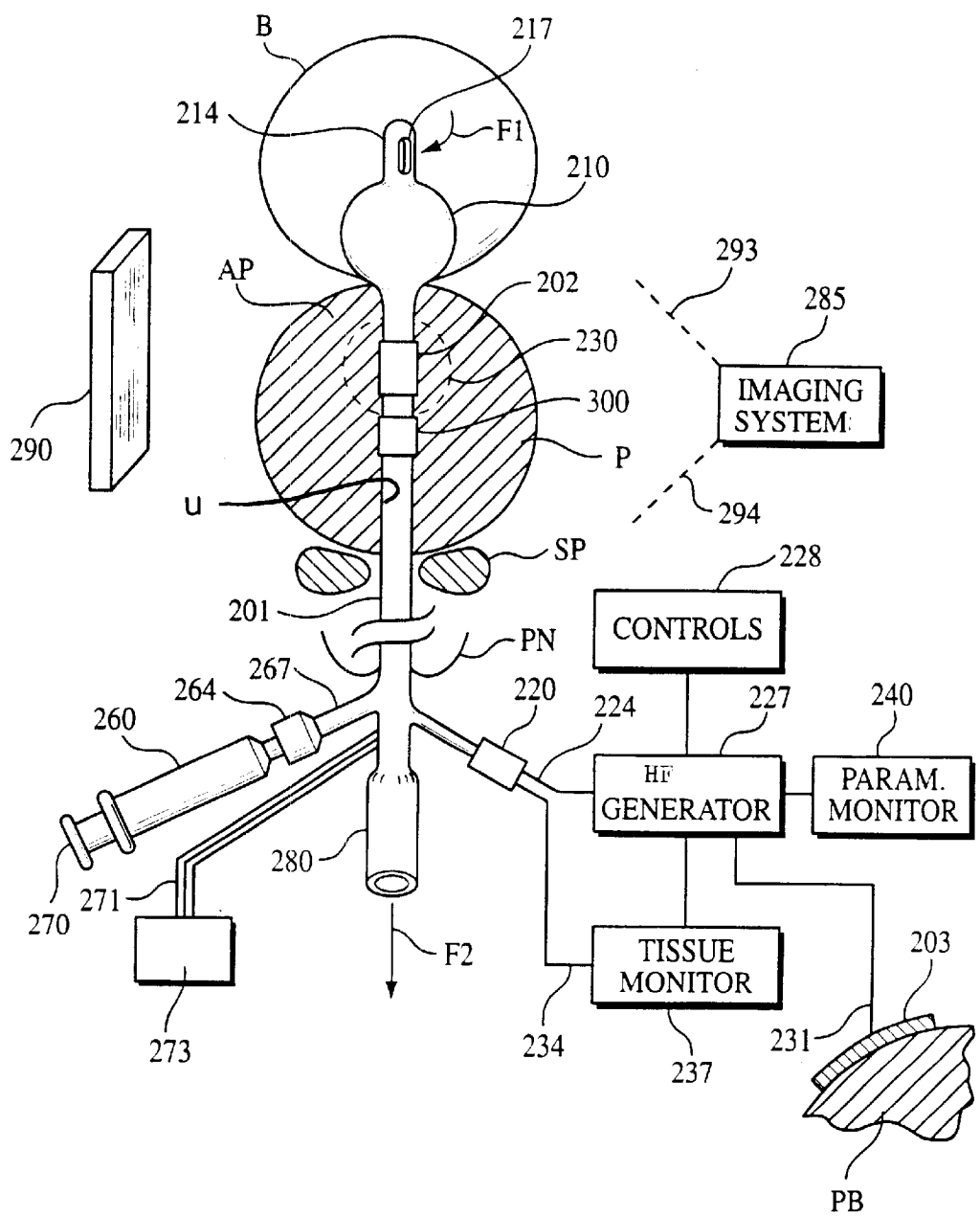
FIG. 1 shows an embodiment of a prostate ablation electrode integrated with a balloon tip catheter with an externally positioned RF electrode and added elements for expanded lesions or temperature sensing in accordance with the present invention.

FIG. 1 shows one embodiment of a system and procedure according to the present invention involving a catheter structure 201, which is passed into the urethra U through the penis PN. The catheter 201 has an RF electrode ring structure 202, which is positioned in prostate P according to clinical needs to alleviate urethral obstruction. At the distal end of the catheter, there is an inflatable balloon structure 210 shown in an inflated state. There is further a distal tip 214 which defines an opening (i.e., port) 217. Urine within bladder B can flow according to an arrow F1 into the opening 217 and out a proximal end of the catheter, as illustrated by an arrow F2.

Rubber catheters with balloon ends are used commonly by urologists. Examples of such catheters are SILASTIC® Foley catheters distributed by the Bard Urological Division of Covington, Georgia.

FIG. 1 shows an embodiment of the present invention in which such a catheter is augmented by the RF ring structure 202 and other components. In the disclosed embodiment, the ring structure 202 is connected internally through the catheter 201 to an RF hub portion 220, a connection cable 224, and a high frequency generator 227. The generator 227 supplies a high frequency electrical signal (e.g., a radio-frequency "RF" signal) to the RF electrode ring structure 202.

The resulting heating of the tissue near the electrode caused by high frequency current dissipating power into the tissue can give rise to an ablation isotherm surface 230 (the dashed line).

Temperature sensors may be located at multiple points along the catheter 201 within the prostate. The temperature sensor may be built inside the catheter or on its surface. The sensor may be a thermistor, thermocouple, or other type of temperature sensor. Temperature signals may be carried by connection wires (e.g., connection 234) extending inside the catheter to an external tissue temperature monitor (represented by tissue monitor 237) to enable thermal monitoring of the ablation process by the clinician as described previously. Specifically, the measured temperature at the sensor is representative of the temperature of the urethra and the nearby prostate tissue.

Alternatively, the tissue monitor 237 could monitor the impedance of the tissue at the ring structures 202 or 300. This can give an indication of location in the prostate or the nature of the RF ablative heating process.

Monitoring of high frequency output parameters from the generator 227 may be accomplished by monitor 240. The monitor 240 may have lesion parameter readouts such as a digital meter reading for display of power, current, voltage, impedance, or other parameters associated with the RF lesion process.

The system in accordance with the present invention, shown in FIG. 1, may be used according to the following illustrated example. The catheter 201 is sterile and disposable. It includes an RF ring structure 202 with hub or connection structures 220, as described above. The catheter 201 is inserted into the penis PN according to common practice until the balloon structure 210 is within the bladder B. The balloon is then inflated by a syringe 260 attached to an inflation hub 264, which is standard on Foley balloon catheters. Inflation by the syringe plunger 270 injects fluid (gas or liquid) into the balloon 210, thereby inflating the balloon and enabling it to be retained within the bladder B. Contrast fluid that is visible on X-ray or fluoroscopic images of the patient's body can be used to inflate the balloon and thus confirm the balloon's position. An internal channel within the catheter 201 communicates the gas or liquid inflation from source 260 to the balloon 210.

Once the catheter is so entrapped within the bladder B by the inflation of the balloon 210, urine within the bladder B can flow according to the arrow F1 through the distal tip opening 217. It can drain through an internal channel and out of the catheter by a catheter hub (i.e., a drain port) 280, as illustrated by the arrow F2. The internal channel within catheter 201 connects the hole 217 at the tip to the drain port 280. With the balloon inflated inside the bladder, X-ray contrast medium may be injected through the hub 280 into the bladder B. An imaging system 285 such as a fluoroscope or X-ray machine can then be used to image the catheter tip 214, the balloon 210, the bladder B, and the RF electrode ring structure 202 together. A separate display device 290 maybe used for providing the image. For example, an X-ray imaging detector may collect X-ray images from X-rays emitted from an X-ray imaging system 285. The detector 290 is within the field of imaging illustrated by the dashed lines 293 and 294. Such X-ray images may be used to verify that the RF electrode 202 is properly placed with respect to the bladder and the prostate P. Imaging machine 285 could alternatively represent a CT, MRI, ultrasound, or other type of imaging device. Safety is increased by imaging confirmation that the RF ring structure 202 is within the prostate at a desired point, typically at the point of urethral obstruction. For example, it may be desired to position the RF electrode 202 sufficiently away from the sphincter SP, which is a critical structure that if ablated could cause incontinence. The imaging step plus the balloon immobilization can help to assure this.

Another step to help secure the catheter and RF electrode in place, and to confirm that placement, is to pull gently (apply traction) on the catheter by the hub 280. This will draw balloon 210 snugly against the bladder neck region AP. It will in turn securely position the RF electrode 202 at its desired position in the prostate P. This is a significant advantage of the present invention because it ensures in a simple way to confirm that the positioning of the catheter is correct and that the catheter will not move. Repeated X-ray contrast injection and imaging is easily done to double check the proper positioning at any time.

Connection of the RF electrode 202 to the high frequency generator 227 can then proceed by the connection 224. The connection 224 runs inside catheter 201 to the electrode element 202 and/or 300. Controls 228 control the power level of the RF output from generator 227 to provide the heat ablation around the RF electrode 202 at the desired levels. Such controls may be manual knobs, automatic processes, computer controls, etc.

The radio-frequency generator 227 may be an electrical unit with, for example, a radio-frequency, microwave, or other high frequency power supply that can deliver a high-frequency electrical signal to the electrode 202. In accordance with known technology for generating radio-frequency (RF) lesions, as described in the Cosman and Goldberg articles described above, a high-frequency signal applied to the exposed electrode 202 generates a heated region around it, which in turn produces a heat lesion or ablation zone 230 around the exposed electrode 202. The size of the ablation zone or heat lesion 230 may be increased by increasing the power that is applied to the tissue from the energy source 227. Thus, the size or volume of the ablation zone 230 can be graded and controlled around the urethral channel.

Also shown is a reference surface electrode 203 which is connected to generator 227 by cable 231 and contacts the patient's body PB (e.g., the patient's skin or other part of the body). (To reduce the complexity of FIG. 1, only a portion of the patient's body PB is shown.) The electrode 203 serves, as is common practice, as a reference or return electrode for the RF current emitted from the RF electrode 202. This is a standard electrical arrangement for so-called monopolar RF ablating (described in the paper by E. R. Cosman cited in the Background section above). Examples of RF lesion generators and RF electrodes using this configuration can be found in the product literature of Radionics, Inc., Burlington, Massachusetts.

A specific illustration of how urinary blockage is reduced in accordance with the system of FIG. 1 follows. By carefully placing the RF electrode within the catheter and positioning the exposed conductive electrode 202 in an appropriate portion of the urethra U where there is a urinary obstruction, an effective ablation of the prostate can be accomplished. By supplying an RF output from the energy source 227 to the electrode 202, heating of the urethra adjacent to the electrode 202 and the surrounding periurethral tissue in the vicinity of the electrode will occur.

When RF energy is delivered from the energy source 227, as in FIG. 1, dissipation of the energy around the RF electrode 202 causes a heating zone to occur around the electrode. This will cause a zone of heat ablation 230, which engulfs the urethra U and the periurethral tissue within the dashed line volume. The zone 230 indicated by the dashed line would, for example, illustrate a typical isotherm surface area or area of constant temperature within which all tissue is raised to a lethal or ablation temperature. An example of a desired temperature for ablation to kill prostate tissue is approximately 50° C. maintained for six minutes. It should be recognized that variations, depending on the desired outcome, are possible.

An ablation isotherm surface, therefore, is an indication of the region in which the cells are dead. At 50° C. or higher temperatures, tissue necrosis is induced in the isotherms within the volume encompassed by the isotherm surface area. Liquefaction of the necrotic tissue occurs within days from the day of treatment. If such an ablation isotherm area (corresponding to ablation or necrosis), as illustrated by the dashed line 230, engulfs the urethra in the region where there is a urethral restriction, then in a matter of days after treatment, the entire periurethral zone, including the urethra within the isotherm surface area, is obliterated and liquefied. The flow of urine from the bladder through the urethra will then carry away the liquefaction and debris from the necrotic tissue away and out of the body through the urethra.

Figure 10:
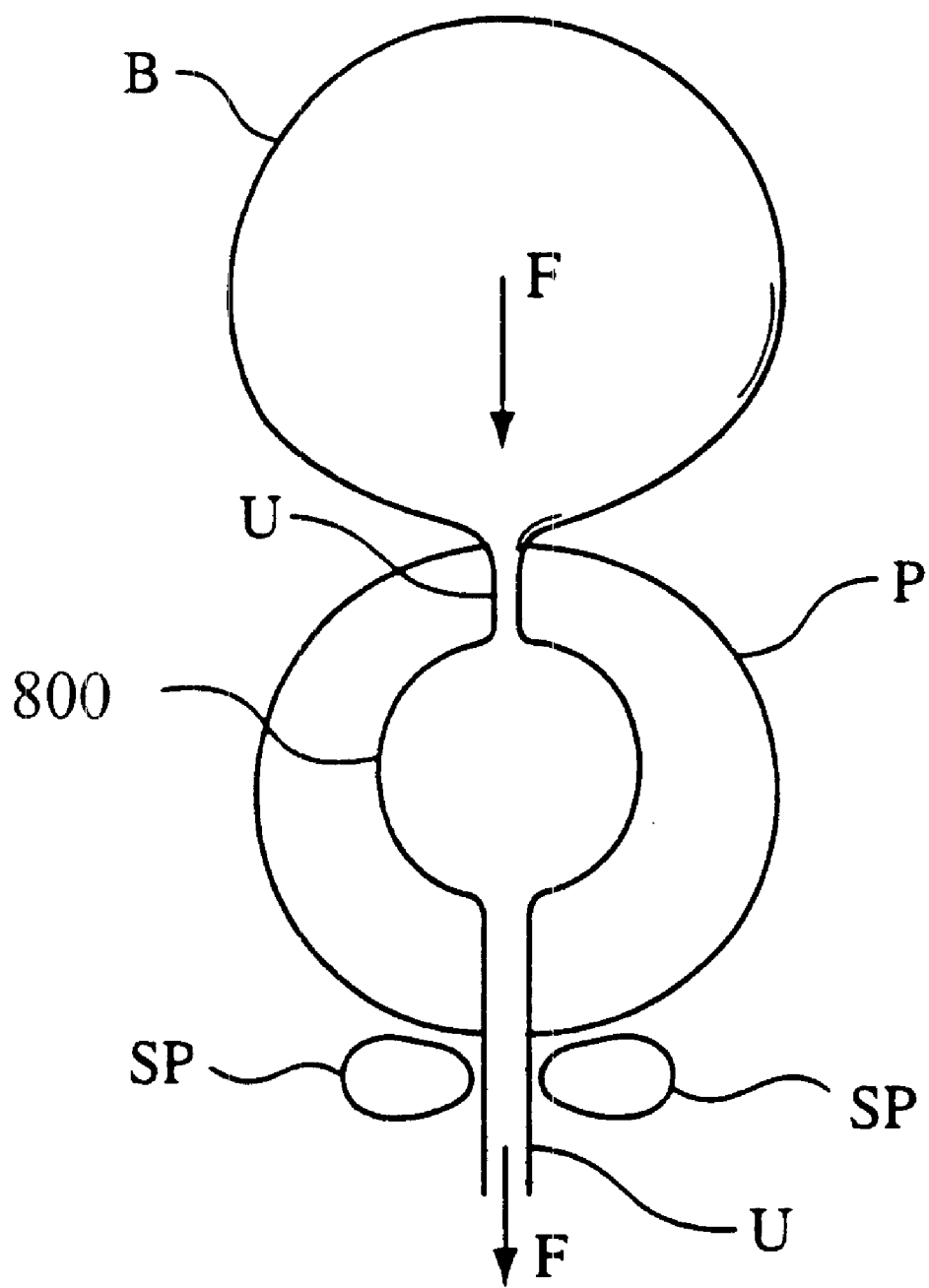
FIG. 10 illustrates a cavity in the prostate contiguous with the urethra induced by a system and method according to the present invention.

FIG. 10 illustrates the effects induced by the system and method for RF urethral enlargement by thermal ablation according to the present invention. The inventive system and procedure obliterates the urethra and region within the ablation isotherm surface boundary to induce a cavity 800. The urethra and prostatic tissue that previously was within this cavity volume has been necrosed and liquefied and passed out through the urethra U by the flow of urine, indicated by the arrows F, from the bladder B out through the penis PN (FIG. 1). The urethral wall has been obliterated to open the channel in communication with the remaining segments of the urethra. The cavity 800 is generally symmetric about the urethra to open a lumenal volume, thereby reducing the restriction of flow that previously existed with the urethral obstruction. Because the cavity 800 is located around the urethra, it is typically axially central to the prostatic gland. There is the advantage that the cavity has a smooth, contiguous continuity with the urethral structures connected to it, increasing the likelihood of laminar fluid flow after the cavity 800 has been formed. Since the cavity is in the periurethral region, the inventive technique also has the advantage that it is remote from various critical structures such as nerves in the outer prostate and the rectal wall.

By way of further explanation, the urethral wall and the periurethral tissue that is in the area of the zone of necrosis is liquefied and carried away by urine flow F. As the urethral cross-sectional area is increased, the impedance to flow of the urine is substantially reduced and the flow vector F is increased in magnitude, restoring normal voiding function or improving voiding rate. The body reacts to this procedure by creating a new epithelial layer of cells, within a matter of a few weeks, to cover the interior surface of the cavity 800.

Because a typical isotherm surface area (in ablation zone 230, FIG. 1) is created in a generally central area of the prostate due to the intra-urethral location of the RF electrode, the peripheral annulus of the prostate acts as a natural margin of safety or thermal buffer zone for the critical organs, which typically lie outside the peripheral region or just outside the prostate. These would include critical nervous structures and the rectum wall and mucosa.

In accordance with one embodiment, a heat lesion of desired size is formed by controlling the temperature of the heated urethra and prostate tissue immediately surrounding the RF electrode 202 to approximately 90° C. At this temperature using, for example, a catheter with a diameter of approximately 2 mm, an ablation volume may be formed having a diameter of approximately 1 to 1.5 cm. This ablation volume will engulf the urethra and the periurethral tissue and be entirely contiguous with the remaining urethra connected to it. The size of the heat lesion is visualizable on CT or MRI image scanning at the same time or after the lesion is made.

In accordance with other embodiments, depending on the lesion sizes desired, other electrode temperatures or prostate tissue temperatures ranging, for example, between 50 and 100° C. are used. The desired lesion sizes are determined (for example 0.3 to 5.0 cm) depending on the size and geometry of the patient's prostate or urethral obstruction or other clinical considerations.

Typically, the energy source 227 has a power range from 0 to approximately 50 watts, although 20 watts or less is generally adequate to achieve the temperatures cited above.

In various embodiments, a typical catheter 201 may have a diameter in the range of 1 to 10 mm to produce lesions of a few centimeters. The width of the electrode may be, for example, between 5 to 60 mm, depending on the application. It should be recognized that varying sizes, geometries, electrode configurations, diameters and lengths, etc. may be used for the RF electrode 202 to produce RF heat lesions.

The catheter 201 may have properties to optimize visualization. For example, a roughened surface on components of the catheter 201 may make it more exogenic and visible in ultrasonic imaging. Furthermore, a metal electrode may be visible in an X-ray image to locate the position of the electrode in the prostate during the procedure.

Alternatively, the catheter may include MRI or CT compatible material so that it is visible in MRI or CT imaging without substantial artifacts. These imaging techniques may be used prior, during, or after the procedure to monitor the placement of the catheter and the progress of the necrotic periurethral cavity after ablation.

The embodiment of FIG. 1 shows the RF electrode ring structure 202 in an intra-urethral position. As discussed above, the heat generated in the tissue near the ring structure 202 produced by connection of the electrode 202 to the generator 227 will ablate and necrose the urethra and periurethral prostatic tissue near the RF electrode ring 202. Also shown on the catheter 201 is a second element 300 which in various embodiments can be a second RF electrode or a temperature sensor. For example, if the region of ablation 230 (the dashed line) needs to be extended to include a region around the electrode 300, then the output from the generator 227 could be applied to the electrode 300. This could be accomplished by a switching system in control unit 228 and appropriate cable connections within connector 224 and 220. This illustrates that multiple RF electrodes can be placed on the same catheter structure 201 to grade the size of the ablation according to clinical needs.

Alternatively, if the structure 300 contains temperature sensors, then the tissue monitor 237 can read out tissue temperature near the structure 300 as an indication of ablation size. For example, if the temperature sensor in 300 reads less than 50° C., then this would indicate that the ablation zone 230 has not reached into the region near the structure 300.

In another example, the impedance of the tissue near elements 202 or 300, or between these elements, could be measured and monitored by the tissue monitor 237. The tissue monitor 237 can be used to determine if the catheter and electrodes are properly placed in the prostate tissue or to determine if the ablation process is complete. Impedance values and changes may indicate the kind of tissue near the electrodes and may indicate if heat ablation has occurred.

In accordance with another embodiment of the present invention, the catheter may not include the temperature sensor. The correlation of an ablation size desired to a certain electrode geometry may be determined by considering RF generator parameters such as power output, voltage, and current. Generally, it can be determined that ablation temperatures of greater than 50° C. in the prostate tissue can be induced, for example, by way of RF power or current levels greater than known amounts. This information can be used by clinicians to induce sufficient ablation sizes to alleviate urinary obstructions by the intra-urethral method, depending on clinical circumstances.

Readout of RF output parameters from the generator 227 can be accomplished by a monitor and display system in the monitor 240 or the generator 227 itself. In various embodiments, this system may involve computers, controls, feedback systems, electronics, and even computer graphic displays to illustrate the parameters by a computer graphic workstation during the progress of the ablation.

In the exemplary embodiment of FIG. 1, the catheter 201 can be made from SILASTICS® rubber, as manufactured by Dow Corning, of Minneapolis, Minnesota. Its diameter is approximately 2 to 8 mm, and its length is in the range of 30 to 40 cm. However, other smaller or larger dimensions may suit varying clinical needs. The electrode structures 202 and 300 can be made from stainless steel rings and bonded to the SILASTIC substrate of the catheter 201. Other materials or plated structures may also be used, including but not limited to Inconel, titanium, or copper plated with gold, or other materials, structures, or metals to suit various clinical needs. The balloon structure and body of the catheter could be similar to the Foley catheter mentioned above with inflatable balloon 210, distal tip 214, port 217, an injection port 264, and the main urinary drainage hub 280. In addition, the hub or other connection 220 for the high frequency and thermal monitoring cabling can be adapted to connect the RF electrode 202 or element 300 to the external devices 227, 228, 237, or 240. Internal connection wires within the SILASTIC rubber body of the catheter 201 connect to the RF electrodes 202 and 300, as well as to temperature sensors within the catheter at various points.

A urological RF catheter, as in FIG. 1, is easily inserted into the urethra and can remain in place within the patient for several days. Diagnostic X-ray images can be taken with an X-ray imaging machine, as illustrated by the X-ray system 285 and the imaging detector 290. This confirms the position of the RF electrode ring 202 in the prostate. Intra-urethral RF ablation is performed when the positioning of the catheter is appropriate, and can be repeated and enlarged as necessary according to the description above. As stated above, the catheter can be left in place in the patient with the balloon inflated for several days after ablation until the ablated zone has fully liquefied. The catheter balloon can then be deflated, and the catheter removed from the urethra, whereupon the necrotic fluid from the ablation zone and the obliterated portion of urethral tissue will be washed away by the urine flow from the bladder B out the urethra.

One advantage of using a catheter-type RF electrode such as the embodiment shown in FIG. 1 is that minimal anesthesia is necessary in inserting the electrode into the urethra. Such catheter structures are familiar to urologists and can be inserted into the patient in the supine position with ease and comfort. A further advantage is that no endoscope is needed to insert it into the urethra or to visualize its position in the prostate. It can be used in an office setting, and not necessarily in a sterile operating room environment, thereby making the procedure more widely available to patients and reducing hospital expenses. It is also relatively economical because it has low construction complexity and can thus be used disposably from a factory-packaged sterile pouch. This is of increasing importance in an increasingly cost conscious medical environment.

Also shown in FIG. 1, as an augmentation of the system, is an external coolant supply 273 with cooling connection(s) 271. This may supply cooled fluid such as saline to flow within a recirculating channel in catheter 201 to cool the electrode 202. Such cooling capability may or may not be included in the balloon catheter depending on clinical needs.

Figure 2:
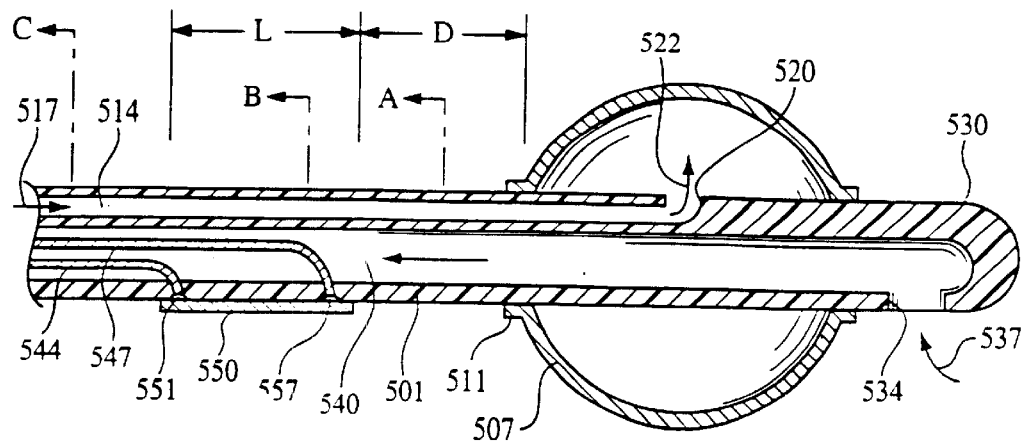
FIG. 2 shows a schematic diagram in partial sectional view of a balloon catheter of FIG. 1 with RF electrode portion, RF connections, and temperature sensors in accordance with the present invention.

Referring now to FIG. 2, a cross-sectional diagram illustrates various aspects of the distal end of a balloon radiofrequency urethral catheter in accordance with the present invention. This sectional view, which shows only the distal section of a catheter embodiment of the present invention, may correspond, for example, to a catheter similar to that in FIG. 1 described above. The catheter body 501 may be made of a rubber material such as silicone. It may be soft and flexible to accommodate the delicate urethral environment. At the distal end is the inflated balloon 507, which also is made of a thin elastic rubber such as silicone. The balloon 507 may be secured in a sealed fashion by joints such as 511 to the catheter material 501. A channel 514 inside the catheter structure 501 allows an inflating fluid such as air or saline to fill the interior of the balloon 507. Injection of the fluid is indicated by the arrow 517, which may correspond to the influx of air as produced by the plunger system 260 in FIG. 1. The channel 514 may connect to the interior of the coupling hose 267 that attaches further to the inflating system 260 in FIG. 1. A side window 520 (i.e., port) in the wall of the catheter, but inside the balloon region, allows the in-flowing air to inflate the balloon, as indicated by the arrow 522.

At the distal tip 530 there is a hole in the body of the tip 534, which may correspond to the hole 217 in FIG. 1. When the catheter is inserted into the urethra and the balloon is secured within the bladder, as shown in FIG. 1, then urine can flow into the hole, as indicated by the arrow 537. An internal channel 540 is constructed within the body 501 of the catheter to allow the flow of the urine backwards towards the hub end of the catheter structure. For example, referring to FIG. 1, the channel 540 may be connected to the proximal hub 280 to allow the outflow of urine, as indicated by arrow F2.

An RF conductive electrode 550 is shown in a location proximal to the balloon 507. It may be, for example, a metal conductive ring-which is bonded to the catheter rubber structure 501 with appropriate silicone cement. The length of the ring is indicated by L in FIG. 2. It is spaced by a distance D from the proximal portion of the balloon 507. The parameters L and D may be specified according to clinical needs and the particular anatomy of the patient being treated. For example, if it is known that a larger lesion is to be made because of a longer portion of urethral obstruction, then the length L could be made longer. The length of the RF electrode may range from one to several millimeters, and even as much as a centimeter, or two, or more. The distance D may also be gauged depending on how far back from the neck of the prostate the heat ablation is desired to be located. D may also be a parameter which is specified according to clinical needs. For example, balloon catheters may come in various model numbers with specification of L and D and the diameter of the catheter body itself according to clinical criteria Also shown in FIG. 2 are wire electrical connections 544 and 547. These connect to or are near to the RF electrode 550. For example, wires 544 may be welded or bonded at point 551 to the RF electrode 550. The wires 544 may provide the connection to the high frequency generator 227 in FIG. 1 (i.e., they are electrically connected to the cable 224). Also, electrical connection wire(s) 547 may be a thermal-sensing or impedance-sensing connection to a point 557 near or on the surface of electrode 550. For example, element 557 may be a thermistor or thermocouple junction, and the connection cables 547 may be electrical connections to a thermal sensor (e.g., tissue monitor 237, FIG. 1) that enables readout of the temperature of prostatic tissue near the RF electrode 550 during the heating process. The electrical connectors 544 and 547, for example, may be directed within the channel 540 and branched through the rubber wall of the catheter at its proximal end to the connection 220, as shown in FIG. 1. Connectors 544 may connect to cables 224, and connections 547 may connect to cables 234 and/or 224. It should be understood that the electrode 550 may consist of several segments as discussed herein. In this case, several connectors (544/547) may be used to connect to each segment of the electrode 550.

Figure 3:
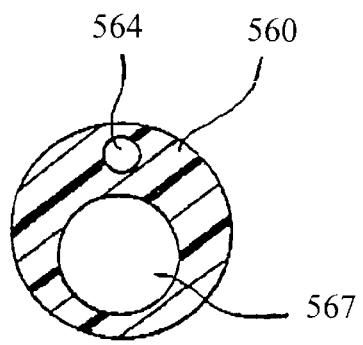
FIG. 3 shows a cross-sectional view of the RF balloon catheter of FIGS. 1 and 2 in accordance with the present invention.

FIG. 3 illustrates a cross-sectional view of the catheter embodiment shown in FIGS. 1 and 2 and through the section plane A indicated in FIG. 2. The catheter in this example is generally of a rounded form comprising the body material 560. The inflation channel within that body is illustrated by 564 and corresponds to the channel 514 in FIG. 2. The draining channel for urine discharge from the bladder is illustrated by 567 and corresponds to the channel 540 in FIG. 2. These channels could be molded within the catheter body 501 of FIG. 2 by extrusion or casting. The two channels 567 and 564 are sufficient to provide urine drainage from the bladder and air-inflation of the balloon, respectively. Uni-directional flow (channel 567) of the urine from the distal to proximal end and a uni-directional flow (channels 564) of the air from the proximal to distal end would implement the drainage and inflation functions. Alternatively, injection of contrast medium into the balloon in the bladder in channel 564 would involve flow from the proximal to distal end of the catheter.

Figure 4:
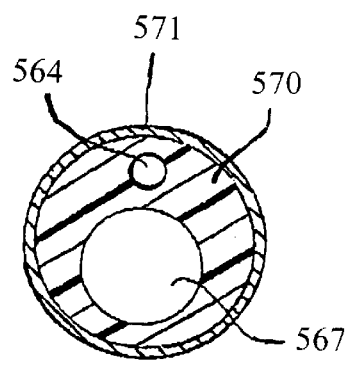
FIG. 4 shows another cross-sectional view of the RF balloon catheter of FIGS. 1 and 2 in accordance with the present invention.

Referring to FIG. 4, a sectional view of the catheter structure of FIG. 1 and FIG. 2 is shown through the sectional plane B of FIG. 2. The silicone rubber body 570 of the catheter is surrounded in this example by the metal ring 571 (which may correspond to electrode 550, FIG. 2). This ring may be a thin stainless steel ring which is bonded by silicone cement to the silicone catheter base 570. It may be made of other materials which suit the clinical need. For example, if the structure is desired to be MRI compatible, the ring could be made of titanium, copper, gold plated copper, or Inconel, depending on the design criteria. Again, the channels 564 and 567 are shown. The RF electrode conductor element 571

(550, FIG. 2) is positioned on the external surface of the catheter structure. Thereby, when inserted into the urethra, the RF electrode 550 will be in direct electrical contact with the urethral tissue immediately adjacent to it (see electrode 202 in FIG. 1). Thus, current from the high frequency generator 227 in FIG. 1, when connected to the catheter, will emanate directly into the adjacent urethral tissue from the RF electrode 550. This will cause radio-frequency or high frequency heating of the urethra and immediately adjacent (peri-urethral) tissue in accordance with the present invention.

Figure 5:
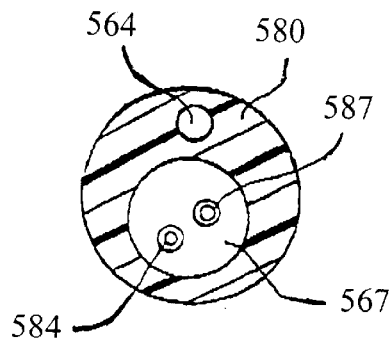
FIG. 5 shows another cross-sectional view of the RF balloon catheter of FIGS. 1 and 2 in accordance with the present invention.

Referring to FIG. 5, a sectional view of the catheter shown in FIG. 2 is illustrated through the plane C of FIG. 2. The rubber flexible body 580 is shown with channel 564 and 567, as described above. The electrical connections 544 and 547, as shown in FIG. 2, are illustrated here in sectional view by the elements 584 and 587, respectively. These electrical connections could be made of a variety of metals and could have multiple electrical strands within them, each insulated one from the other. The connections may contain copper, stainless steel, braided metal, thermocouple junction wires, or other electrical materials with appropriate insulation to suit the construction and clinical needs. For example, if flexibility and strength are needed to produce the electrical connection to the RF electrode 550 in FIG. 2, then structure 584 may be a stainless steel braided wire together with a copper electrical conductor to produce low impedance and structurally sound connection. Element 587 may provide connections to a temperature sensor, in which case a bi-metal pair of thermocouple wires may be used, each separated one from the other.

It is noted that various types and configurations of RF electrode structures are possible. For example, instead of a solid metal ring, element 550 in FIG. 2 could be a spiral wound or braided electrical wire structure and fixed onto the external surface of the catheter or built into the underlying substrate of rubber body 501. The catheter may have embedded in it wires within the rubber portion 501 to form a mesh or braid of exposed electrical elements to produce a similar RF conductive electrode surface.

Figure 6:
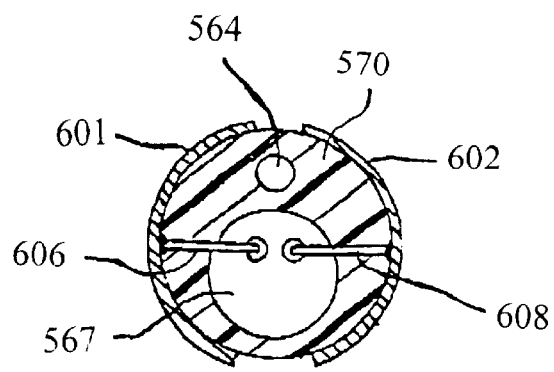
FIG. 6 shows another cross-sectioned view of an RF balloon catheter with a multi-sector electrode in accordance with the present invention.

FIG. 6 shows another embodiment of the invention wherein rather than a continuous circular, cylindrical ring, such as illustrated in FIG. 2 and FIG. 4, the RF element could be sectors 601 and 602 of a ring bonded onto the surface of the body 570 in FIG. 4. These annular sectors, therefore, could give directional selectivity to the heating of the urethra and surrounding prostate. For example, a left semi-circle 601 and right semi-circle 602 could be present instead of the continuous circular ring in FIG. 4. If each semi-ring is connected to the opposite poles of the output of generator 227 in FIG. 1, then there would be a bipolar electrical configuration. Accompanying independent electrical connection wires 606 and 608, analogous to wire 547 in FIG. 2, within the body 501 of the catheter could make connection from the generator 227 to the independent bipolar electrode surfaces of 601 and 602, as just described.

Figure 7:
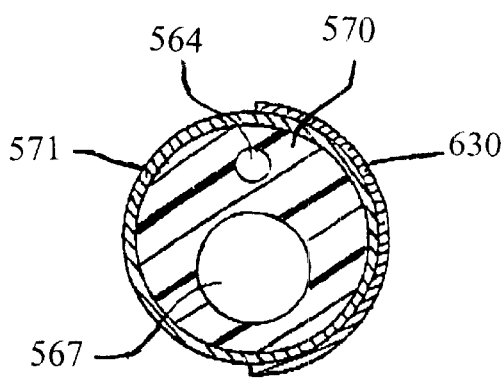
FIG. 7 shows another cross-sectioned view of an RF balloon catheter with an asymmetrical electrode in accordance with the present invention.

FIG. 7 shows another variant on the construction of the example shown in FIG. 2 and FIG. 4 in which the cylindrical ring 571 is insulated on a portion of its area by the insulation layer 630. When connected to the RF generator, this would project the radio-frequency current into the surrounding tissue through the exposed portion of ring 571 to one particular azimuthal angle (the left side of the catheter as viewed in FIG. 7) relative to the catheter body 570. Thus selective heating in the particular direction may be implemented. The insulation layer 630 may be constructed of, for example, plastic, Teflon, polyurethane, polyethylene or some other type of insulating coating or sheet.

As another embodiment of the invention, multiple radio-frequency electrode conductive sectors such as 550 in FIG. 2 may be placed along the elongated length of the catheter 501. For example, several rings (or portions of rings) such as ring 202 or 300 in FIG. 1 may be present that are spaced apart in the longitudinal direction of the catheter. They may have independent electrical connections analogous to the connection 544 (and/or 547) to ring 550 in FIG. 2. The clinician may then have the option of connecting one or more or a variety of patterns of the electrical rings to produce smaller or larger or more selective heat ablations of the urethra and the prostate surrounding it. The application of output from the generator 227 to a multiplicity of such rings spaced in known positions along the catheter may be controlled by the controller 228 in FIG. 1. Thus the size, length, and depth of the heat ablation within the urethra and the periurethral tissue may be graded and changed according to clinical needs.

Again, as shown in FIG. 1, other electrical rings such as 300 could be present on the catheter. This would also require electrical connections, which could be run along the elongated length of the catheter from the distal electrodes, to the proximal hub, and out to external apparatus. Such connections might comprise additional radio-frequency connectors to the generator, impedance monitoring connections to an impedance monitor, or thermo-sensing connections to thermal sensors in the catheter. Such electrical connections could also be drawn through the channel 540 of FIG. 2. Alternatively, all of the electrical connections as shown in FIG. 2 could be embedded within the walls of the rubber catheter structure itself, and become an integral part of the cross-sectional structure rather than being passed through fluid (liquid or air) channels within the structure. In a further alternative embodiment, a separate channel could be placed within the catheter to house only the electrical connections. A variety of geometric and configurational variations are possible to construct catheters in accordance with the present invention by those skilled in the art of making such implant catheters.

Figure 8:
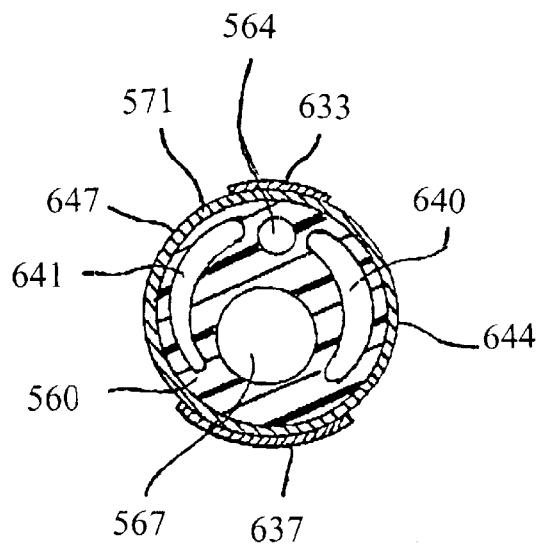
FIG. 8 shows another embodiment of the present invention having a catheter with internal cooling channels and segmented RF electrodes.

Referring to FIG. 8, an alternative embodiment of the present invention is shown as illustrated by a cross-sectional view through a catheter such as in FIG. 1 in which cooling channels are introduced into the catheter structure to enable cooling of the RF electrode portions. For example, in the catheter as shown in FIGS. 1 and 2, it may be desired in certain situations to enlarge a lesion size within the prostate and therefore to have the option of cooling the RF electrode ring 571 or not cooling the RF electrode ring 571. In this way, for example, a urethral and periurethral lesion can be made by not cooling the ring 571, and previously or subsequently an enlarged lesion may be made to engulf more of the prostate by cooling the exposed portions of the RF electrode ring 571 during the application of RF power to the prostate. Construction of cooled RF electrodes has been described by Goldberg et al. and referred to in the Background section above. The catheter in FIG. 1 may have added ports at or near the hub end 280 to accommodate circulation of coolant fluid into the catheter from an external coolant supply 273 and through internal cooling channels, as shown in FIGS. 1 and 8.

As illustrated in FIG. 8, the catheter body is illustrated as for example through section B in FIG. 2. The catheter body 560 again is made of a flexible rubber. The balloon inflation channel 564 and urine drainage channel 567 are present, as above. A conductive, surface mounted RF electrode ring 571 is cemented to the body 560, as in the previous examples. In addition in this embodiment, added channels 640 and 641 are shown in cross-sectional view. Channel 640 may carry cooling fluid from the proximal hub to the region of the distal RF electrode, and channel 641 may carry the coolant fluid back from the RF electrode to the proximal hub. Illustration of coolant connection 271 and coolant supply 273 are shown in FIG. 1. The two channels may be connected within the catheter near the catheter's distal end to enable the fluid recirculation. This circulation process thereby would cool the exposed RF electrode surfaces that are in contact with the urethral tissue. For example, in the embodiment of FIG. 8, there are insulated portions 633 and 637 which cover a portion of the electrode ring 571. The exposed electrical surfaces 644 and 647 are then sectors along the ring. The proximity of the cooling channels 640 and 641 will cool the exposed surfaces 644 and 647, respectively. Thus, if an enlarged lesion is desired within the prostatic tissue, the RF power can be applied as in the examples above, thereby heating the tissue in proximity and at a distance from surfaces 644 and 647. The degree of power can be increased and the degree of urethral ablation enlarged by use of the cooling channels 460 and 461. By reference, the use of cooled RF electrodes is described in the papers of Goldberg, as cited above.

In a situation where only a urethral and near urethral tissue ablation is desired, cooling channels such as those shown in FIG. 8 are not necessary or may not be used to circulate coolant. As for example in the examples of FIGS. 2, 3, 4, 5, 6, and 7, a more simplified internal channel structure with only balloon inflation and urinary drainage channels are shown, which will reduce the complexity and the cost of such a balloon type RF ablation urethral electrode.

It is further noted that if a balloon type distal end for the catheter electrode is not present, as described in several embodiments of the parent application, then the catheter cross-sectional structures become even simpler. If there are no inflation or drainage channels within the catheter and no cooling channels within the catheter, then there can be no need for any such channels at all. The electrical connections, as shown in the above figures for the radio-frequency connection, temperature connection, impedance monitoring, etc., may be either embedded directly in the flexible rubber of the catheter or they may be passed through an internal channel whose function is to allow such electrical connections to be assembled within the catheter in the manufacturing process.

Figure 9:
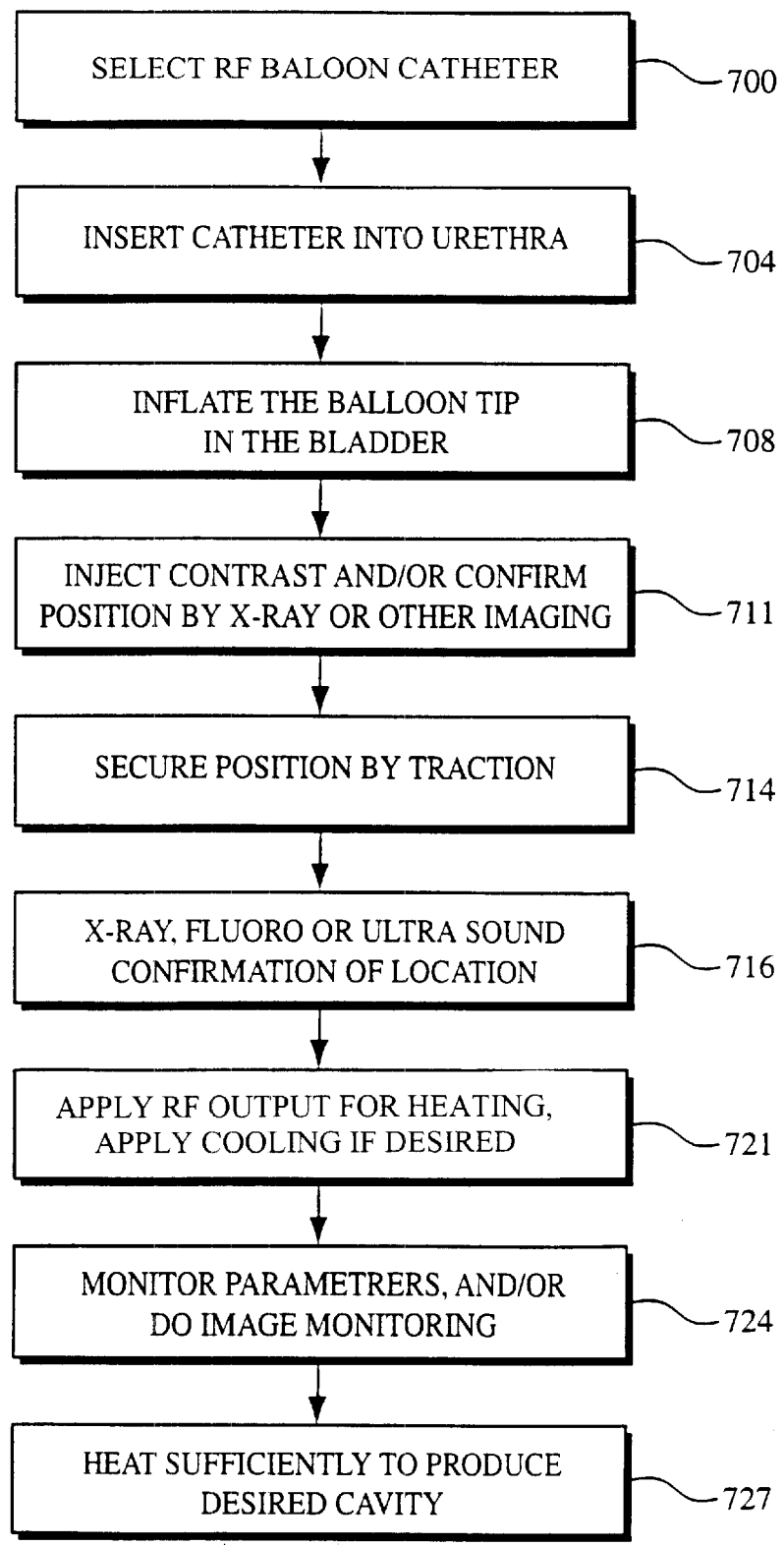
FIG. 9 shows a flow chart of a process employed in operating a system in accordance with the present invention.

Referring now to FIG. 9, a flow chart is shown to illustrate the process of intra-urethral RF ablation using a balloon catheter for relief of urinary obstruction. The procedure starts by selecting the appropriate RF balloon catheter (step 700). This may involve selecting the diameter, length, balloon size, ring dimensions and positions, use of multi-ring balloon catheter, use of catheters with temperature sensing, impedance monitoring rings, multiple temperature sensors along its longitudinal length, and other specifications of the balloon catheter, some of which have been described above in connection with FIGS. 1 through 8. For example, by knowledge from diagnostic imaging of the size of the patient's prostate and the position of the obstruction, the appropriate length of RF electrode segment L, as shown in FIG. 2, as well as its separation D from the balloon, as shown in FIG. 2, may be selected. For this purpose, the catheters may come packaged with particular dimensions of L, D, catheter diameter, catheter length, etc. to suit specific clinical needs.

The next step may be insertion of the catheter into the urethra (step 704). Insertion of catheters is a common technique and can involve use of Foley-type catheters for urine drainage. During this step, diagnostic imaging such as ultrasound, CT, MRI, or X-rays may be used to monitor the position and depth of the catheter. For this purpose, the catheters as shown in FIGS. 1 through 8 above may be in part radiopaque or have radiopaque markings on them so that their tip position and electrode position can be visualizable in X-ray, CT, MR, or other types of imaging.

Referring further to FIG. 9, once it is determined that the tip end of the catheter is properly within the patient's bladder, the balloon tip may be inflated within the patient's bladder (step 708 in FIG. 9). This step may be followed by further imaging (e.g., ultrasound, CT, MR, fluro, or X-ray diagnostic imaging) to confirm that the balloon is properly placed. For example, in step 711 of FIG. 9, a radiopaque contrast medium (contrast agent) is injected into the bladder through, for example, the hub 280 in FIG. 1 so that it emanates from the port opening 217 in FIG. 1 to produce a radiopaque contrast of the bladder (step 711). In this way, the position of the balloon within the bladder and against the neck AP in FIG. 1 can be confirmed. Alternatively, step 708 may involve inflating the balloon with radiopaque contrast fluid for X-ray confirmation.

The balloon may be secured in its position by applying traction or gentle pulling (step 714 in FIG. 9) so that the balloon fits snugly against the neck of the prostate and bladder junction. At this point, the RF electrode ring 202 is at a known position relative to the neck of the bladder. That position may be pre-selected by the dimension D, as shown in FIG. 2. This is a simply implemented but important safety step to assure the proper location of the RF electrode with respect to the prostate prior to making a heat ablation.

At this point, further X-ray, fluoroscopic, ultrasound, or other imaging confirmation may be used to verify that the RF electrode and the balloon are in the proper place (step 716). When this confirmation is made, the connections to the external RF generator may be made as shown in FIG. 1, and the output from the generator 227 of FIG. 1 may then be delivered through the catheter connections to the RF electrode 202 in FIG. 1 (step 721).

As the heat ablation process begins, the ablative destruction of the urethra and periurethral tissue will begin and increase near the position of the RF electrode. This process can be monitored by observing the high frequency generator parameters on monitoring device 240 in FIG. 1 (step 724 of FIG. 9). Various other tissue monitoring such as temperature sensing and impedance monitoring at the RF electrode or ancillary rings such as 300 in FIG. 1 may be carried out in this step 724. The control of the RF generator may be done manually, automatically, or by computer, as in the control unit 228 of FIG. 1.

In step 727 of FIG. 9, the clinician determines the sufficiency of the heat ablation to produce the desired clinical effect of reducing urinary obstruction. This will be based on his experience, the visualization of the ablation parameters, and the particular clinical situation.

To elaborate further on the steps of making the heat ablation, the step 721 of FIG. 9 can involve elevating the voltage, current, or power applied by the high frequency generator. The generator may have manual controls such as knobs or other elements to control its output levels that can be actuated at this point. Alternatively, the process may be automated with a set power or temperature level predetermined on the generator control system and an automatic or semi-automatic achievement of that high frequency control parameter reached by an appropriate feedback and control system within the generator. These elements can all be built into the energy source 227, for example, illustrated in FIG. 1.

The actual parameters of the RF power delivered to the RF electrode within the urethra may be recorded and monitored (step 724). Parameters of interest can include the temperature recorded at the RF electrode, the temperatures recorded at satellite electrodes, for example which can be placed in the prostate, rectum, or other neighboring bodily locations within the operative field. Other recorded parameters can be the RF power, current, voltage, impedance, and so on. The time of RF power application may also be monitored in step 724. A predetermined set time of exposure of the RF power to the electrode may be desirable, depending on clinical needs. The duration of heating may depend on the reading of temperature sensors in the prostate or the RF electrode at various positions. Knowledge of these RF parameters and the geometry and size of the RF electrode can assist in guiding the surgeon as to the size of the lesion and resultant urethral/prostatic cavity that will be produced. For example, it may be known from clinical experience that certain size ablations can be induced for certain electrode geometry types with a known value of RF power, current or voltage. Alternatively, a known ablation temperature as recorded in one or more of the temperature monitors, sustained for a desired time, may be the criterion for ending the ablation process. As represented in FIG. 9, these parameters may be monitored during the ablation process and influence the decision of the clinician to terminate or continue the process according to experience and parameter values. By reference, the measurement of parameters is illustrated by use of lesion generator systems of Radionics (Burlington, Massachusetts). For example, the model RFG3C lesion generator sold by Radionics, Inc. provides impedance monitoring similar to that discussed above. It should be appreciated that other forms of tissue monitoring may be used. For example, oxygen levels or ionic concentration as are known in the art may be measured.

The decision on the adequacy of the duration and parameter settings to achieve the correct RF heat ablation effect on the prostate that is sufficient to reduce urinary obstruction is determined at step 727 of FIG. 9. The decision to stop the procedure when it is believed that the cavity is adequate may also be made at this step.

In accordance with one embodiment of the present invention, the clinician may choose an RF electrode geometry of a certain size, diameter, and length. The clinician may know from experience that insertion of such catheter-electrode intra-urethrally, the electrode having a built-in temperature sensor, and delivering RF power to raise the measured temperature at the electrode to a certain temperature value will produce a known and generally adequate ablation cavity to alleviate urinary obstruction.

In accordance with another embodiment of the present invention, the RF electrode may not include a temperature sensor. The correlation of ablation size desired for a given electrode geometry may be determined by considering RF parameters such as power, output, voltage, and current. Generally, it can be determined that ablation temperatures greater than 50° C. in the prostate tissue can be induced, for example, by RF power or RF current levels greater than known amounts. In that embodiment, desired levels for these RF power and current parameters may be achieved by the clinician for a desired duration of RF power application to alleviate the urinary obstruction by creating a sufficient intra-urethral cavity. It is understood that there may be a variable range of these parameters, time durations, and electrode geometries according to the experience acquired by clinicians to achieve adequate ablation cavities.

In accordance with one embodiment of the present invention, if CT, MR, or other imaging techniques are used during ablation, then they may be used to monitor or to decide on adequate ablation size. This is included as an alternative or added monitoring step in block 724. For example, certain MR images can be used to visualize the thermal distribution around the electrode, and thus to indicate the desired end-point for a prostate ablation.

An added or alternative process in accordance with the present invention is to perform an RF heat ablation together with cooling the electrode by circulation of coolant inside the balloon catheter. This is indicated as an added or alternative step as part of step block 721 in FIG. 9.

The use of intra-urethral RF electrodes herein has the advantages of simplicity, economy, control, consistency, reproducibility, and patient tolerance compared to other techniques such as TURP, TUNA, and TUMT aimed at treating BPH or prostate cancer. The present system and method maintains the RF electrode within the urethra, and does not pierce the urethral wall. As described, the heat ablation process using an intra-urethral electrode according to the invention has the effect in one of the embodiments of ablating the urethral wall and periurethral tissue to open the channel and to destroy the urethra near the electrode. This has advantages over other methods and apparatus which seek to leave the urethra intact or unablated, such as TUNA, McGahan et al.'s procedure, and TUMT cited above. In the present invention, because the electrode does not pierce the urethra, the risk of hemorrhage is reduced. Furthermore, with the RF electrode within the urethra, and with use of imaging control as described above, there is a more exact knowledge of the ablation zone in the central prostate region to reduce the chance of damaging sensitive structures. Thus, with patients in whom bleeding is a problem, such as those in frail health on anti-coagulation medication for cardiac or neurological disorders, the present intra-urethral approach has an advantage over approaches such as TURP and TUNA where deliberate scraping, cutting, or piercing of the urethra will cause irritation and bleeding.

A further advantage of the present invention is that there is more precise control of the placement of the electrode (e.g., 202) in the prostate and increased safety against heat ablation of the wrong tissue region. In the various embodiments, the position of the electrode may be determined by placement of the balloon tip in the bladder. This, in turn, may ensure that the electrode is correctly positioned in relation to the prostate, bladder neck, and sphincter. This is measurable by the catheter parameters selected as described above and visualizable with ultrasound, X-ray, CT, or MRI. Therefore, the positioning and extent of the ablation zone is better controlled with the present invention than with other systems and methods. Furthermore, because the system and method of the present invention locates the ablative cavity in the central periurethral region of the prostate, the risk of damage to critical structures such as the rectal mucosa, the rectal wall, neural structures, or seminal channels is reduced.

A further advantage of the present system and method is that it enables direct widening of the urethral channel without preserving the urethra itself. This is in contrast to the TUNA procedure, the technique of McGahan, and the TUMT procedure in which preservation of the urethra itself is a primary objective. In one embodiment of the present invention, an objective is destruction of the urethra near the site of the RF electrode. This has the advantage that the region of necrosis, including the urethra and surrounding prostatic tissue, will be liquefied and swept away by the urine passing through the urethra without the possibility of entrapment of coagulated tissue or necrotic material outside of the urethra. Such entrapment is possible in the technique of TUNA, McGahan, or TUMP, where regions of ablation and necrosis are outside the intact urethra. This can cause swelling of the tissue around the urethra as absorption of necrotic tissue proceeds, resulting in continued pressure to the urethra and further closing down of the urethral channel. These other techniques have the further disadvantage that an increase in osmotic particles within the interstitial prostatic medium can take days or weeks to absorb, resulting in extended irritation, swelling, urinary obstruction, and risk. By contrast, in the present invention, this post-ablation debris is naturally swept away in the urethral cavity and contiguous urethral stream, thus avoiding the above-mentioned disadvantages of other techniques.

Because it is better tolerated and of less risk and expense than TURP, TUNA, TUMT, and non-central radio-frequency lesion making (viz. McGahan, et al.), the present invention is indicated for a wider population of patients, and potentially will achieve more effective clinical results. Also, the present system and method widens the urethral channel, as does, for example, TURP, but does so without the side effects of bleeding. Also, the present invention has the advantage over the TURP or TUNA techniques in that it requires only minimal anesthetic and no hospitalization. Therefore, the present invention will be far better tolerated by patients, especially those who are in frail health and for whom a TURP procedure may be too risky to endure.

The present system and method of intra-urethral ablation has the further advantage of safety compared to TURP, TUNA, TUMT, or non-central lesion approaches (such as McGahan, et al.). Urologists are trained to do catheter placements in the urethra, so that the catheter and electrode placement of the present system and method is natural and safe for them to perform. The electrode placement being visualizable and mechanically determinable in the present invention has the advantage of simple and certain control compared to TURP, TUNA, TUMT, or non-central RF lesion techniques for which the electrode position or location of ablation is less definite in some cases. Minimal anesthetic is required for the present invention, which is not the case for TURP, where bleeding and discomfort is significant. Minimizing anesthetic is important since its administration and consequences are not risk free, especially for patients in fragile health. The use of a flexible catheter is easily tolerated by the patient and enables an exact positioning of the RF electrode within the prostatic body, yielding safer knowledge of the ablative cavity position.

Yet another advantage of the present invention is that the ablation cavity is made contiguous to and central to (in the case of a symmetric electrode) the stream of the urethral passage. Thus, the urethral enlargement is a smooth, symmetrically placed cavity. This will produce a more laminar flow of the urine from the bladder through the urethra, which in turn will reduce the turbulence and possibility of pockets of stagnation of fluid in the widened region of the prostatic passage.

Yet a further advantage of the present system and method is that the electrode system and process of use is simple and more economical than for the TURP, TUNA, and TUMT techniques. This will lead to a less expensive procedure than TURP, TUNA, or TUMT procedures, making it amenable to and more cost effective for a wider patient population. The use of a flexible balloon RF catheter, as one embodiment cited above, has the advantage of economy and simplicity of structure. It can be provided as a disposable device that ensures sterility and cleanliness for each application.

Yet a further advantage of the present invention is that the electrode construction and geometry is simpler and less expensive than the electrode structure for a cooled microwave catheter, as used in TUMT. For example, in the exemplary embodiments of FIGS. 1 through 7, only two channels are required. One channel is for inflation of the balloon. The other channel is for drainage of urine from the bladder or alternatively injection of contrast media into the bladder. In the case of TUMT, where cooling of the catheter and electrode is an objective, further channels within the catheter must be present to enable circulation of coolant fluid. For example, a channel which carries the fluid from the proximal end of the catheter to the distal tip would be needed and another channel which carries the recirculated fluid from the distal tip to the proximal end must be built into the TUMT catheter structure. Such extra circulation channels for cooling fluid can be built into the present invention structure as illustrated above, but it is not a requirement in the situation where cooling of the electrode is not desired. When cooling of the balloon electrode is required, added channels (as illustrated in FIG. 8 above) can be introduced to recirculate coolant near the surface mounted RF electrode portion. The present invention has the further advantage that heat ablation of the urethra and the prostate can be done to widen the urethral channel and also another ablation step can be made with circulating coolant of the electrode and nearby tissue to enlarge the region of heat ablation or to augment the ablation zone in desired directions.

Forms and embodiments of the intra-urethral radio-frequency urethral ablation system and method are provided involving various electrode designs with and without temperature monitoring, and in various electrode geometries. However, it should be recognized that other obvious forms may be used. For example, various materials, configurations, and control and display systems can be employed in a system or method for performing intra-urethral prostate ablation, with or without the capability of cooling the electrode, without departing from the scope of the invention.

In view of these considerations, as would be apparent by persons skilled in the art, implementations and system should be considered broadly and with reference to the claims set forth below:

What is claimed is:

1. A method of relieving urethral obstruction in a patient having a urethra, a prostate and a bladder, the method comprising the steps of:
   providing a catheter that comprises:
      an electrically conductive active sector electrode disposed on an outer surface of the catheter, and
      an inflatable balloon proximate to a distal end of the catheter wherein the inflatable balloon may be inflated by injection of fluid through a port in the catheter;
   inserting the catheter into the urethra of the patient a distance sufficient to provide contact between the electrode and at least a portion of the urethra and to insert the balloon into the bladder of the patient;
   inflating the balloon;
   positioning the electrode within the urethra of the patient at a location proximate the prostate where urethral enlargement is desired; and
   applying a high-frequency signal to the electrode to elevate the temperature of the urethra to at least 50° C.

to induce heat ablation of at least a portion of the urethra and at least a portion of periurethral tissue in the patient, thereby inducing ablative reduction of tissue mass of the urethra and nearby tissue to reduce the urethral obstruction.

2. The method of claim 1 wherein the positioning step further comprises the step of viewing an operative field within the patient to position the electrode relative to the obstruction.

3. The method of claim 1 further comprising the step of measuring a temperature of tissue proximate the electrode.

4. The method of claim 1 further comprising the step of measuring an impedance of tissue proximate the electrode.

5. The method of claim 1 wherein the step of providing the cather includes providing the electrode with a plurality of electrically conductive areas separated by at least one electrical insulator.

6. The method of claim 1 wherein the step of providing the catheter includes providing the catheter defining two internal channels that are adapted to carry fluid, a first one of the two internal channels having a port at a proximal end of the catheter to allow inflow of fluid to inflate the balloon, and a second one of the two internal channels having a distal opening at a distal end of the catheter and a proximal opening at a proximal end of the catheter to allow drainage of urine from the bladder of the patient when the catheter is inserted into the urethra and the balloon is inflated in the bladder.

7. The method of claim 1 wherein applying the signal includes enlarging the passageway relative to a normal size of the urethral passage.

8. The method of claim 1 wherein applying the signal includes applying an output through the electrode to a return electrode.

9. The method of claim 1 wherein the electrode is a non-cooled electrode.

10. A method of treating the urethral passage, comprising:

placing a distal portion of an elongate member intraurethrally into the urethral passage, the elongate member having a circumferential, electrically conductive sector electrode disposed on an outer surface of the distal portion of the elongate member and arranged about a portion of a circumference of the elongate member, and energizing the electrode with high frequency energy to elevate the temperature of the urethra to at least 50° C. to ablate tissue of a wall defining the urethral passage and ablate adjacent prostate tissue to form a cavity communicating with the urethral passage.

11. The method of claim 10 wherein energizing the electrode forms a cavity in the wall and adjacent prostate tissue having a diameter in the range of about 0.3 to 5 cm.

12. The method of claim 10 wherein energizing the electrode elevates a temperature of the wall and adjacent prostate tissue to about 50 to 100° C.

13. The method of claim 12 wherein energizing the electrode includes elevating the temperature for about six minutes.

14. The method of claim 10 wherein energizing the electrode includes connecting the electrode to a high frequency generator.

15. The method of claim 10 wherein energizing the electrode includes forming the cavity such that the urethral passage is enlarged relative to a normal size of the urethral passage.

16. The method of claim 10 wherein energizing the electrode includes applying the high frequency energy through the electrode to a return electrode.

17. The method of claim 10 further comprising imaging the electrode to monitor the position of the electrode.

18. The method of claim 17 wherein imaging includes ultrasonic imaging.

19. The method of claim 18 wherein imaging includes inserting an ultrasonic scanner transrectally.

20. The method of claim 17 wherein imaging includes CT imaging.

21. The method of claim 17 wherein imaging includes MR imaging.

22. The method of claim 10 further comprising detecting a temperature level of tissue surrounding the electrode.

23. The method of claim 10 further comprising providing the elongate member with multiple, circumferential, electrically conductive sector electrodes at the distal portion.

24. The method of claim 23 wherein energizing the electrode includes energizing the multiple sector electrodes in a bi-polar configuratior.

25. The method of claim 23 wherein providing includes affixing an electric insulator over a portion of a ring electrode to form the sector electrodes.

26. The method of claim 10 wherein the electrode is a non-cooled electrodes.

27. A method of treating the urethral passage, comprising:

placing a distal portion of an elongate member intraurethrally into the urethral passage, the elongate member having a plurality of electrically discrete sector electrodes arranged about a portion of a circumference of the elongate member, and energizing the electrodes with high frequency energy to ablate tissue of a wall defining the urethral passage and adjacent prostate tissue.

28. The method of claim 27 wherein energizing the electrodes with high frequency energy includes elevating the temperature of tissue of a wall defining the urethral passage to at least 50° C.

29. The method of claim 27 wherein the electrodes are non-cooled electrodes.

* * * * *

UNITED STATES PATENT AND TRADEMARK OFFICE
CERTIFICATE OF CORRECTION

PATENT NO. : 6,447,505 B2
DATED : September 10, 2002
INVENTOR(S) : Francis J. McGovern et al.

It is certified that error appears in the above-identified patent and that said Letters Patent is hereby corrected as shown below:

<u>Title page,</u>
Item [56], U.S. PATENT DOCUMENTS, insert

| -- 2,407,690 | 9/1946  | Southworth      | 128/422    |
| 4,116,198    | 9/1978  | Roos            | 128/303.15 |
| 4,184,492    | 1/1980  | Meinke et al.   | 128/303.14 |
| 4,682,596    | 7/1987  | Bales et al.    | 128/303.14 |
| 4,967,765    | 11/1990 | Turner et al.   | 128/785    |
| 4,979,948    | 12/1990 | Geddes et al.   | 606/33     |
| 5,007,437    | 4/1991  | Sterzer         | 428/786    |
| 5,061,266    | 10/1991 | Hakky           | 606/15     |
| 5,112,330    | 5/1992  | Nishigaki et al.| 606/46     |
| 5,178,620    | 1/1993  | Eggers et al.   | 606/41     |
| 5,220,927    | 6/1993  | Astrahan et al. | 128/785    |
| 5,277,201    | 1/1994  | Stern           | 607/98     |
| 5,301,687    | 4/1994  | Wong et al.     | 606/41     |
| 5,304,214    | 4/1994  | DeFord et al.   | 607/105    |
| 5,322,507    | 6/1994  | Costello et al. | 128/4      |
| 5,454,809    | 10/1995 | Janssen         | 606/41     |
| 5,509,929    | 4/1996  | Hascoet et al.  | 607/101    |
| 5,697,909    | 12/1997 | Eggers et al.   | 604/114    |
| 5,733,315    | 3/1998  | Burdette et al. | 607/97     |
| 5,810,764    | 9/1998  | Eggers et al.   | 604/23     |
| 5,891,134    | 4/1999  | Goble et al.    | 606/27     |
| 5,944,715    | 8/1999  | Goble et al.    | 606/41 --  |

After, FOREIGN PATENT DOCUMENTS, insert

| -- WO | WO 91/13650    | 9/1991   |
| WO    | WO 97/00646    | 1/1997   |
| WO    | WO 97/00647    | 1/1997   |
| WO    | WO 97/28840    | 8/1997   |
| EP    | EP 0 754 437 A2| 1/1997 --|

UNITED STATES PATENT AND TRADEMARK OFFICE
CERTIFICATE OF CORRECTION

PATENT NO. : 6,447,505 B2
DATED : September 10, 2002
INVENTOR(S) : Francis J. McGovern et al.

It is certified that error appears in the above-identified patent and that said Letters Patent is hereby corrected as shown below:

After, OTHER PUBLICATIONS, insert

-- Brochure, SMK Sluijter-Mehta Kits, "The Finest Radiofrequency Electrodes for Pain Therapy", Radionics, Burlington, MA 1996.
Costello et al., "Nd:YAG Laser Ablation of the Prostate as a Treatment for Benign Prostatic Hypertrophy", *Lasers in Surgery and Medicine*, vol. 12, No. 2; pp. 121-124, 1992.
Harada et al., "Microwave Surgical Treatment of Diseases of Prostate" *Urology*, vol. XXVI, No. 6, pp. 572-576, December 1985.
Kramolowsky, et al., "The Urological Application of Electrosurgery," *The Journal of Urology*, vol. 146, pp. 669-674, September 1991.
Kramolowsky, et al., "Use of 5f Bipolar Electrosurgical Probe in Endoscopic Urological Procedures," *The Journal of Urology*, vol. 143, 275-277, February 1990.
McGahan et al., "Percutaneous Ultrasound-Guide Radiofrequency Electrocautgery Ablation of Prostate Tissue in Dogs" *Acad Radiol.*, vol. 2, pp. 61-65, 1994.
Nardella, "Radio Frequency Energy and Impedance Feedback," *SPIE*, vol. 1068, pp. 42-48, 1989.
*Radionics Neurosurgical Instruments*, Trigeminal Neralgia Kit Description, 1981.
Tucker, et al., "A Comparison of Urologic Application of Bipolar Versus Monopolar Five French Electrosurgical Probes," *The Journal of Urology*, vol. 141, pp. 662-665, March 1989. --

Column 1,
Line 57, "one" should read -- One --.

Column 6,
Lines 12-13, "anti coagulation" should read -- anticoagulation --.
Line 17, "periurethral-region" should read -- periurethral region --.

Column 8,
Line 67, "maybe" should read -- may be --.

Column 13,
Line 63, "ring-which" should read -- ring which --.

UNITED STATES PATENT AND TRADEMARK OFFICE
CERTIFICATE OF CORRECTION

PATENT NO. : 6,447,505 B2
DATED : September 10, 2002
INVENTOR(S) : Francis J. McGovern et al.

It is certified that error appears in the above-identified patent and that said Letters Patent is hereby corrected as shown below:

Column 14,
Line 13, "criteria" should read -- criteria. --.

Column 24,
Line 32, "configuratior" should read -- configuration --.
Line 37, "electrodes" should read -- electrode --.

Signed and Sealed this

Nineteenth Day of August, 2003

JAMES E. ROGAN
*Director of the United States Patent and Trademark Office*